US008230457B2

(12) United States Patent
Lee et al.

(10) Patent No.: US 8,230,457 B2
(45) Date of Patent: Jul. 24, 2012

(54) METHOD AND SYSTEM FOR USING COHERENCE OF BIOLOGICAL RESPONSES AS A MEASURE OF PERFORMANCE OF A MEDIA

(75) Inventors: Hans C. Lee, Carmel, CA (US); Timmie T. Hong, San Diego, CA (US); William H. Williams, Hilo, HI (US); Michael R. Fettiplace, Madison, WI (US)

(73) Assignee: The Nielsen Company (US), LLC., Schaumburg, IL (US)

( * ) Notice: Subject to any disclaimer, the term of this patent is extended or adjusted under 35 U.S.C. 154(b) by 304 days.

(21) Appl. No.: 11/804,517

(22) Filed: May 17, 2007

(65) Prior Publication Data
US 2008/0222670 A1   Sep. 11, 2008

Related U.S. Application Data

(60) Provisional application No. 60/905,184, filed on Mar. 7, 2007.

(51) Int. Cl.
*H04N 7/16* (2011.01)
(52) U.S. Cl. ............... 725/10; 725/9; 382/118
(58) Field of Classification Search ................ None
See application file for complete search history.

(56) References Cited

U.S. PATENT DOCUMENTS

| | | | |
|---|---|---|---|
| 4,695,879 A * | 9/1987 | Weinblatt | ............. 725/10 |
| 4,755,045 A | 7/1988 | Borah et al. | |
| 4,846,190 A | 7/1989 | John | |
| 4,931,934 A | 6/1990 | Snyder | |
| 4,974,602 A | 12/1990 | Abraham-Fuchs et al. | |
| 5,243,517 A | 9/1993 | Schmidt et al. | |
| 5,406,957 A | 4/1995 | Tansey | |
| 5,447,166 A | 9/1995 | Gevins | |

(Continued)

FOREIGN PATENT DOCUMENTS

KR   10-2000-0072489   12/2000

(Continued)

OTHER PUBLICATIONS

Form PCT/ISA/220, PCT/US07/15019, "PCT Notification of Transmittal of The International Search Report and the Written Opinion of the International Searching Authority, or the Declaration," 1 pg.

(Continued)

*Primary Examiner* — Kristine Kincaid
*Assistant Examiner* — Oschta Montoya
(74) *Attorney, Agent, or Firm* — Hanley, Flight & Zimmerman, LLC

(57) ABSTRACT

Various embodiments of the present invention create a novel system for rating an event in a media based on the strength of the emotions viewers feel towards the event. The viewer's responses to the media can be measured and calculated via physiological sensors. The metric for rating the strength of the media is created based on the mathematical coherence of change (up or down) of all pertinent physiological responses across multiple viewers. Such rating offers an objective ability to compare the strengths of events of the media, as there is a strong correlation between high coherence of physiological responses (all viewers feel the same thing at the same time) and strong ratings of emotionality, engagement, likeability, success in the marketplace/on screen.

31 Claims, 9 Drawing Sheets

U.S. PATENT DOCUMENTS

| | | | |
|---|---|---|---|
| 5,450,855 A | 9/1995 | Rosenfeld | |
| 5,579,774 A | 12/1996 | Miller et al. | |
| 5,601,090 A | 2/1997 | Musha | |
| 5,676,138 A | 10/1997 | Zawilinski | |
| 5,692,906 A | 12/1997 | Corder | |
| 5,724,987 A | 3/1998 | Gevins et al. | |
| 5,740,812 A | 4/1998 | Cowan | |
| 5,774,591 A | 6/1998 | Black et al. | |
| 5,983,129 A | 11/1999 | Cowan et al. | |
| 5,983,214 A * | 11/1999 | Lang et al. | 707/1 |
| 6,099,319 A | 8/2000 | Zaltman et al. | |
| 6,254,536 B1 | 7/2001 | DeVito | |
| 6,292,688 B1 | 9/2001 | Patton | |
| 6,309,342 B1 | 10/2001 | Blazey et al. | |
| 6,322,368 B1 | 11/2001 | Young et al. | |
| 6,585,521 B1 * | 7/2003 | Obrador | 434/236 |
| 6,623,428 B2 | 9/2003 | Miller et al. | |
| 6,626,676 B2 | 9/2003 | Freer | |
| 6,652,283 B1 | 11/2003 | Van Schaack et al. | |
| 6,656,116 B2 | 12/2003 | Kim et al. | |
| 6,678,866 B1 | 1/2004 | Sugimoto et al. | |
| 6,792,304 B1 | 9/2004 | Silberstein | |
| 6,839,682 B1 | 1/2005 | Blume | |
| 6,978,115 B2 | 12/2005 | Whitehurst et al. | |
| 7,035,685 B2 | 4/2006 | Ryu et al. | |
| 7,050,753 B2 | 5/2006 | Knutson | |
| 7,113,916 B1 | 9/2006 | Hill | |
| D565,735 S | 4/2008 | Washbon | |
| 7,739,140 B2 * | 6/2010 | Vinson et al. | 705/10 |
| 2001/0016874 A1 | 8/2001 | Ono et al. | |
| 2001/0056225 A1 | 12/2001 | DeVito | |
| 2002/0154833 A1 | 10/2002 | Koch et al. | |
| 2002/0182574 A1 | 12/2002 | Freer | |
| 2003/0003433 A1 | 1/2003 | Carpenter et al. | |
| 2003/0063780 A1 * | 4/2003 | Gutta et al. | 382/118 |
| 2003/0076369 A1 | 4/2003 | Resner | |
| 2003/0081834 A1 | 5/2003 | Philomin et al. | |
| 2003/0093784 A1 * | 5/2003 | Dimitrova et al. | 725/10 |
| 2003/0126593 A1 | 7/2003 | Mault | |
| 2003/0153841 A1 | 8/2003 | Kilborn et al. | |
| 2004/0018476 A1 | 1/2004 | Ladue | |
| 2004/0039268 A1 | 2/2004 | Barbour et al. | |
| 2004/0072133 A1 | 4/2004 | Kullock et al. | |
| 2004/0208496 A1 | 10/2004 | Pilu | |
| 2004/0267141 A1 | 12/2004 | Amano et al. | |
| 2005/0010087 A1 | 1/2005 | Banet | |
| 2005/0043774 A1 | 2/2005 | Devlin et al. | |
| 2005/0045189 A1 | 3/2005 | Jay | |
| 2005/0066307 A1 | 3/2005 | Patel et al. | |
| 2005/0071865 A1 | 3/2005 | Martins | |
| 2005/0097594 A1 * | 5/2005 | O'Donnell et al. | 725/15 |
| 2005/0113656 A1 | 5/2005 | Chance | |
| 2005/0172311 A1 | 8/2005 | Hjelt et al. | |
| 2005/0289582 A1 * | 12/2005 | Tavares et al. | 725/10 |
| 2006/0258926 A1 | 11/2006 | Ali et al. | |
| 2006/0277102 A1 | 12/2006 | Agliozzo | |
| 2006/0293921 A1 | 12/2006 | McCarthy et al. | |
| 2007/0053513 A1 | 3/2007 | Hoffberg | |
| 2007/0055169 A1 | 3/2007 | Lee et al. | |
| 2007/0060830 A1 | 3/2007 | Le et al. | |
| 2007/0060831 A1 | 3/2007 | Le et al. | |
| 2007/0066914 A1 | 3/2007 | Le et al. | |
| 2007/0116037 A1 | 5/2007 | Moore | |
| 2007/0168461 A1 | 7/2007 | Moore | |
| 2007/0173733 A1 | 7/2007 | Le et al. | |
| 2007/0179396 A1 | 8/2007 | Le et al. | |
| 2007/0184420 A1 | 8/2007 | Mathan et al. | |
| 2007/0225585 A1 | 9/2007 | Washbon et al. | |
| 2007/0235716 A1 | 10/2007 | Delic et al. | |
| 2007/0238945 A1 | 10/2007 | Delic et al. | |
| 2007/0265507 A1 | 11/2007 | De Lemos | |
| 2008/0091512 A1 | 4/2008 | Marci et al. | |
| 2008/0144882 A1 | 6/2008 | Leinbach et al. | |
| 2008/0159365 A1 | 7/2008 | Dubocanin et al. | |
| 2008/0177197 A1 | 7/2008 | Lee et al. | |
| 2008/0211768 A1 | 9/2008 | Breen et al. | |
| 2008/0218472 A1 | 9/2008 | Breen et al. | |
| 2009/0024049 A1 | 1/2009 | Pradeep et al. | |
| 2009/0024447 A1 | 1/2009 | Pradeep et al. | |
| 2009/0024448 A1 | 1/2009 | Pradeep et al. | |
| 2009/0024449 A1 | 1/2009 | Pradeep et al. | |
| 2009/0024475 A1 | 1/2009 | Pradeep et al. | |
| 2009/0025023 A1 | 1/2009 | Pradeep et al. | |
| 2009/0030287 A1 | 1/2009 | Pradeep et al. | |
| 2009/0030303 A1 | 1/2009 | Pradeep et al. | |
| 2009/0030717 A1 | 1/2009 | Pradeep et al. | |
| 2009/0030930 A1 | 1/2009 | Pradeep et al. | |
| 2009/0036755 A1 | 2/2009 | Pradeep et al. | |
| 2009/0036756 A1 | 2/2009 | Pradeep et al. | |
| 2009/0062629 A1 | 3/2009 | Pradeep et al. | |
| 2009/0062681 A1 | 3/2009 | Pradeep et al. | |
| 2009/0063255 A1 | 3/2009 | Pradeep et al. | |
| 2009/0063256 A1 | 3/2009 | Pradeep et al. | |
| 2009/0082643 A1 | 3/2009 | Pradeep et al. | |
| 2009/0083129 A1 | 3/2009 | Pradeep et al. | |
| 2009/0105576 A1 | 4/2009 | Do et al. | |
| 2009/0112077 A1 | 4/2009 | Nguyen et al. | |
| 2009/0156925 A1 | 6/2009 | Jin et al. | |
| 2009/0214060 A1 | 8/2009 | Chuang et al. | |
| 2009/0222330 A1 | 9/2009 | Leinbach | |

FOREIGN PATENT DOCUMENTS

| | | |
|---|---|---|
| KR | 10-2001-0104579 | 11/2001 |

OTHER PUBLICATIONS

Form PCT/ISA/210, PCT/US07/15019, "PCT International Search Report," 2 pgs.

Form PCT/ISA/237, PCT/US07/15019, "PCT Written Opinion of the International Searching Authority," 5 pgs.

Form PCT/IB/326, PCT/US07/015019, "Notification Concerning Transmittal of International Preliminary Report on Patentability."

Form PCT/IB/373, PCT/US07/15019, "International Preliminary Report on Patentability."

Form PCT/ISA/220, PCT/US07/14955, "PCT Notification of Transmittal of the International Search Report and the Written Opinion of the International Searching Authority, or the Declaration," 1 pg.

Form PCT/ISA/210, PCT/US07/14955, "PCT International Search Report," 2 pgs.

Form PCT/ISA/237, PCT/US07/14955, "PCT Written Opinion of the International Searching Authority," 6 pgs.

Form PCT/IB/326, PCT/US07/14955, "Notification Concerning Transmittal of International Preliminary Report on Patentability." 1 page.

Form PCT/IB/373, PCT/US07/14955, "International Preliminary Report on Patentability." 1 page.

Form PCT/ISA/220, PCT/US07/16796, "PCT Notification of Transmittal of the International Search Report and the Written Opinion of the International Searching Authority, or the Declaration," 1 pg.

Form PCT/ISA/210, PCT/US07/16796, "PCT International Search Report," 2 pgs.

Form PCT/ISA/237, PCT/US07/16796, "PCT Written Opinion of the International Searching Authority," 6 pgs.

Form PCT/IB/326, PCT/US07/16796, "Notification Concerning Transmittal of International Preliminary Report on Patentability." 1 page.

Form PCT/IB/373, PCT/US07/16796, "International Preliminary Report on Patentability." 1 page.

Form PCT/ISA/220, PCT/US06/31569, "PCT Notification of Transmittal of the International Search Report and the Written Opinion of the International Searching Authority, or the Declaration," 1 pg.

Form PCT/ISA/210, PCT/US06/31569, "PCT International Search Report," 3 pgs.

Form PCT/ISA/237, PCT/US06/31569, "PCT Written Opinion of the International Searching Authority," 6 pgs.

Form PCT/IB/326, PCT/US06/31569, "Notification Concerning Transmittal of International Preliminary Report on Patentability." 1 page.

Form PCT/IB/373, PCT/US06/31569, "International Preliminary Report on Patentability." 1 page.

Form PCT/ISA/220, PCT/US07/20714, "PCT Notification of Transmittal of the International Search Report and the Written Opinion of the International Searching Authority, or the Declaration," 1 pg.

Form PCT/ISA/210, PCT/US07/20714, "PCT International Search Report," 2 pgs.
Form PCT/ISA/237, PCT/US07/20714, "PCT Written Opinion of the International Searching Authority," 6 pgs.
Form PCT/IB/326, PCT/US07/20714, "Notification Concerning Transmittal of International Preliminary Report on Patentability." 1 page.
Form PCT/IB/373, PCT/US07/20714, "International Preliminary Report on Patentability." 1 page.
Form PCT/ISA/220, PCT/US07/17764, "PCT Notification of Transmittal of the International Search Report and the Written Opinion of the International Searching Authority, or the Declaration," 1 pg.
Form PCT/ISA/210, PCT/US07/17764, "PCT International Search Report," 2 pgs.
Form PCT/ISA/237, PCT/US07/17764, "PCT Written Opinion of the International Searching Authority," 7 pgs.
Form PCT/IB/326, PCT/US07/17764, "Notification Concerning Transmittal of International Preliminary Report on Patentability." 1 page.
Form PCT/IB/373, PCT/US07/17764, "International Preliminary Report on Patentability." 1 page.
Form PCT/ISA/220, PCT/US07/20713, "PCT Notification of Transmittal of the International Search Report and the Written Opinion of the International Searching Authority, or the Declaration," 1 pg.
Form PCT/ISA/210, PCT/US07/20713, "PCT International Search Report," 2 pgs.
Form PCT/ISA/237, PCT/US07/20713, "PCT Written Opinion of the International Searching Authority," 5 pgs.
Form PCT/IB/326, PCT/US07/20713, "Notification Concerning Transmittal of International Preliminary Report on Patentability." 1 page.
Form PCT/IB/373, PCT/US07/20713, "International Preliminary Report on Patentability." 1 page.
Form PCT/ISA/220, PCT/US08/09110, "PCT Notification of Transmittal of the International Search Report and the Written Opinion of the International Searching Authority, or the Declaration," 1 pg.
Form PCT/ISA/210, PCT/US08/09110, "PCT International Search Report," 3 pgs.
Form PCT/ISA/237, PCT/US08/09110, "PCT Written Opinion of the International Searching Authority," 4 pgs.
Form PCT/ISA/220, PCT/US08/75640, "PCT Notification of Transmittal of the International Search Report and the Written Opinion of the International Searching Authority, or the Declaration," 1 pg.
Form PCT/ISA/210, PCT/US08/75640, "PCT International Search Report," 2 pgs.
Form PCT/ISA/237, PCT/US08/75640, "PCT Written Opinion of the International Searching Authority," 3 pgs.
Form PCT/ISA/220, PCT/US08/78633, "PCT Notification of Transmittal of the International Search Report and the Written Opinion of the International Searching Authority, or the Declaration," 1 pg.
Form PCT/ISA/210, PCT/US08/78633, "PCT International Search Report," 2 pgs.
Form PCT/ISA/237, PCT/US08/78633, "PCT Written Opinion of the International Searching Authority," 6 pgs.
Form PCT/ISA/220, PCT/US08/82147, "PCT Notification of Transmittal of the International Search Report and the Written Opinion of the International Searching Authority, or the Declaration," 1 pg.
Form PCT/ISA/210, PCT/US08/82147, "PCT International Search Report," 2 pgs.
Form PCT/ISA/237, PCT/US08/82147, "PCT Written Opinion of the International Searching Authority," 13 pgs.
Form PCT/ISA/220, PCT/US08/82149, "PCT Notification of Transmittal of the International Search Report and the Written Opinion of the International Searching Authority, or the Declaration," 1 pg.
Form PCT/ISA/210, PCT/US08/82149, "PCT International Search Report," 2 pgs.
Form PCT/ISA/237, PCT/US08/82149, "PCT Written Opinion of the International Searching Authority," 14 pgs.
Form PCT/ISA/220, PCT/US08/75651, "PCT Notification of Transmittal of the International Search Report and the Written Opinion of the International Searching Authority, or the Declaration," 1 pg.
Form PCT/ISA/210, PCT/US08/75651, "PCT International Search Report," 2 pgs.
Form PCT/ISA/237, PCT/US08/75651, "PCT Written Opinion of the International Searching Authority," 9 pgs.
Form PCT/ISA/220, PCT/US08/85723, "PCT Notification of Transmittal of the International Search Report and the Written Opinion of the International Searching Authority, or the Declaration," 1 pg.
Form PCT/ISA/210, PCT/US08/85723, "PCT International Search Report," 2 pgs.
Form PCT/ISA/237, PCT/US08/85723, "PCT Written Opinion of the International Searching Authority," 7 pgs.
Form PCT/ISA/220, PCT/US08/85203, "PCT Notification of Transmittal of the International Search Report and the Written Opinion of the International Searching Authority, or the Declaration," 1 pg.
Form PCT/ISA/210, PCT/US08/85203, "PCT International Search Report," 2 pgs.
Form PCT/ISA/237, PCT/US08/85203, "PCT Written Opinion of the International Searching Authority," 6 pgs.
Form PCT/ISA/220, PCT/US08/75649, "PCT Notification of Transmittal of the International Search Report and the Written Opinion of the International Searching Authority, or the Declaration," 1 pg.
Form PCT/ISA/210, PCT/US08/75649, "PCT International Search Report," 3 pgs.
Form PCT/ISA/237, PCT/US08/75649, "PCT Written Opinion of the International Searching Authority," 5 pgs.
Technology Platform: SmartShirt + Eye-Tracking Innerscope Research, Mar. 2007.
Egner, Tobias; Emilie Strawson, and John H. Gruzelier, "EEG Signature and Phenomenology of Alpha/theta Neurofeedback Training Versus Mock Feedback." Applied Psychophysiology and Biofeedback. vol. 27, No. 4. Dec. 2002.
Clarke, Adam R. et al., EEG Analysis of Children with Attention-Deficit/Hyperactivity Disorder and Comorbid Reading Disabilities, Journal of Learning Disabilities, vol. 35, No. 3, (May-Jun. 2002), pp. 276-285.
Carter, R., "Mapping the Mind" 1998 p. 182 University of California Press, Berkley.
Harmony et al. (2004) Specific EEG frequencies signal general common cognitive processes as well as specific tasks processes in man. Int. Journal of Psychophysiology 53(3): 207-16.
Klimesch, W., Schimke, H., Schwaiger, J. (1994) Episodic and semantic memory: an analysis in the EEG theta and alpha band. Electroencephalography Clinical Neurophysiology.
Mizuhara, H.,Wang LQ, Kobayashi, K., Yamaguchi, Y., (2004) A long range cortical network emerging with theta oscillation in mental task. Neuroreport 15(8): 1233-1238.
Seldon, G (1981) "Machines that Read Minds." Science Digest, Oct.
Willis, M. & Hodson, V.; Discover Your Child's Learning Style: Children Learn in Unique Ways—Here's the Key to Every Child's Learning Success, Prime Publishing. Roseville, CA.
Wise, A (1996) The High Performance Mind, Mastering Brainwaves for Insight, Healing and Creativity. G.P. Putnam's Son, New York. pp. 13-15; 20-22; 143-156.
Wise, A (1996) The High Performance Mind, Mastering Brainwaves for Insight, Healing and Creativity. G.P. Putnam's Son, New York. pp. 156-158; 165-170; 186-187, 189-192.
El-Bab, M. (2001) Cognitive event related potentials during a learning task. Doctoral Dissertation, Faculty of Medicine, University of Southampton, UK.
Gevins et al. (1997) High resolution EEG mapping of cortical activation related to a working memory, Cereb Cortex. 7: 374-385.
Hughes, J.R. & John, E.R. (1999) Conventional and Quantitative Electroencephalography in Psychiatry. Journal of Neuropsychiatry and Clinical Neurosciences. vol. 11(2): 190-208.

* cited by examiner

METHOD AND SYSTEM FOR USING COHERENCE OF BIOLOGICAL RESPONSES AS A MEASURE OF PERFORMANCE OF A MEDIA

RELATED APPLICATIONS

This application claims priority to U.S. Provisional Patent Application No. 60/905,184, filed Mar. 7, 2007, and entitled "A Method and system for using coherence of biological responses as a measure of performance of a section of media," by Hans C. Lee, et. al., and is hereby incorporated herein by reference.

This application is related to and cross-references U.S. patent application Ser. No. 11/804,555, filed concurrently, and entitled "A method and system for rating media and events in media based on physiological data," by Hans C. Lee, et. al., the contents of which application are hereby incorporated by reference.

BACKGROUND

1. Field of Invention

This invention relates to the field of media performance rating based on physiological responses from viewers.

2. Background of the Invention

Prior methods and systems for calculating how viewers respond to a media often include taking an average response from a survey and/or adopting viewer "knobs" or other rating schemes. These prior methods show only what the average response is, not how individuals respond. Just as individuals' responses can be strongly biased by prior experienced personal events, their responses to an event in the media can also be influenced by a previous event that happened directly before the current event. This effect can heavily skew the average response to the current event in a manner not directly related to the current event. Consequently, by just taking the average of physiological responses across individual viewers into account at a given time, the prior approaches may be biased by subjective responses of viewers and are incapable of capturing the whole picture of how viewers feel when they view the media, as individual outlier responses dominate the average response.

SUMMARY OF INVENTION

Various embodiments of the present invention create a novel system and method for rating an event in a media based on the strength of the emotions viewers feel towards the event. The viewers' responses to the media can be measured and calculated via physiological sensors. The metric for rating the strength of the media is created based on the mathematical coherence of change (up or down) of all pertinent physiological responses across the viewers. Such rating offers an objective ability to compare the strengths of events of the media, as there is a strong correlation between high coherence of physiological responses (all viewers feel the same thing at the same time) and strong ratings of emotionality, engagement, likeability, and success in the marketplace/on screen.

DETAILED DESCRIPTION OF EMBODIMENTS OF THE INVENTION

The invention is illustrated by way of example and not by way of limitation in the figures of the accompanying drawings in which like references indicate similar elements. It should be noted that references to "an" or "one" or "some" embodiment(s) in this disclosure are not necessarily to the same embodiment, and such references mean at least one.

Various embodiments of the present invention create a method and system to rate the performance of a media using the coherence of physiological responses across groups of viewers of the media. The coherence of response metric objectively measures the strength of the media across many people as it shows when viewers feel the same emotions at the same time. Compared to the survey data or average value of physiological responses, the coherence of the physiological responses corresponds to viewers either having the same emotional responses at the same time, or having different ones at the same time, which is a much better indicator of performance of the media.

The rating approach of the present invention is based on the principle that, in the marketplace, a media that performs strongly is not only capable of creating strong emotional responses in one viewer, but is also capable of creating the same strong emotional responses across many viewers. Viewers feel different emotions while they watch a piece of media, but for a successful media, there are key events in the media that create a coherent response in physiological data across groups of viewers. A media will not perform well if there is no coherent response to the media; i.e., the media will not sell well because of bad ratings, bad word of mouth or other negative views if some viewers really like the media while other comparable viewers do not.

Figure 1:
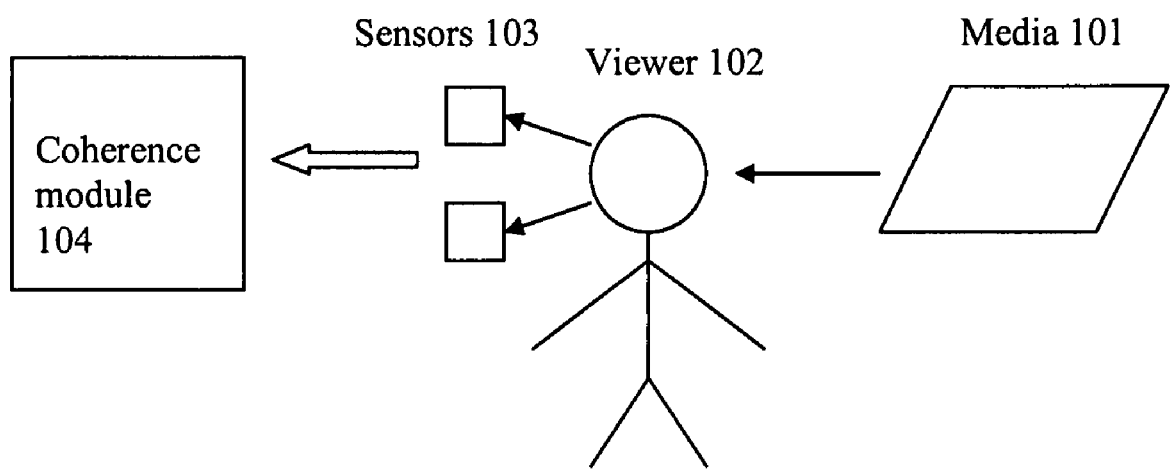
FIG. 1 is an illustration of an exemplary system for rating a media based on coherence of physiological responses from viewers in accordance with one embodiment of the present invention.

FIG. 1 is an illustration of an exemplary system for rating a media based on coherence of physiological responses from viewers in accordance with one embodiment of the present invention. Although this diagram depicts components as functionally separate, such depiction is merely for illustrative purposes. It will be apparent to those skilled in the art that the components portrayed in this figure can be arbitrarily combined or divided into separate software, firmware and/or hardware components. Furthermore, it will also be apparent to those skilled in the art that such components, regardless of how they are combined or divided, can execute on the same computing device or multiple computing devices, and wherein the multiple computing devices can be connected by one or more networks.

Referring to FIG. 1, one or more sensors 103 are utilized to measure and record physiological data of each of a plurality of viewers 102, who are watching an event of a media 101. Here, the media can be one or more of a movie, a video, a television program, a television commercial, an advertisement, a video game, an interactive online media, a print, and any other media from which a viewer can learn information or be emotionally impacted. The duration of the event in the media can be constant, non-linear, or semi-linear in time. The physiological data measured can include but is not limited to, heart rate, electroencephalogram (EEG) signals, blink rate, breathing, motion, and each of the one or more sensors can be one of: an electroencephalogram, an accelerometer, a blood oxygen sensor, a galvanometer, an electromygraph, and any other physiological sensor. Alternatively, an integrated sensor headset can be adopted as discussed in details later. Physiological data in the body have been shown to correlate with emotional changes in humans. By sensing these exact changes instead of using surveys, knobs or other easily biased measures of response, the present invention improves both the data that is recorded and the granularity of such data as physiological responses can be recorded many times per second.

Once measured, the physiological data of the viewers can be transmitted to a coherence module 104, which derives physiological responses of the viewers based on their physiological data measured while they were watching the event. Here, the physiological response can be one or more of: thought, liking, engagement, immersion, physical engagement, valence, and vigor, wherein thought and liking can be calculated from EEG. Coherence of the viewers' physiological responses to the event can then be calculated and the event can be rated based on the coherence of the physiological responses from the viewers. Optionally, the media itself can also be rated based on the ratings of all the events in the media.

Figure 2:
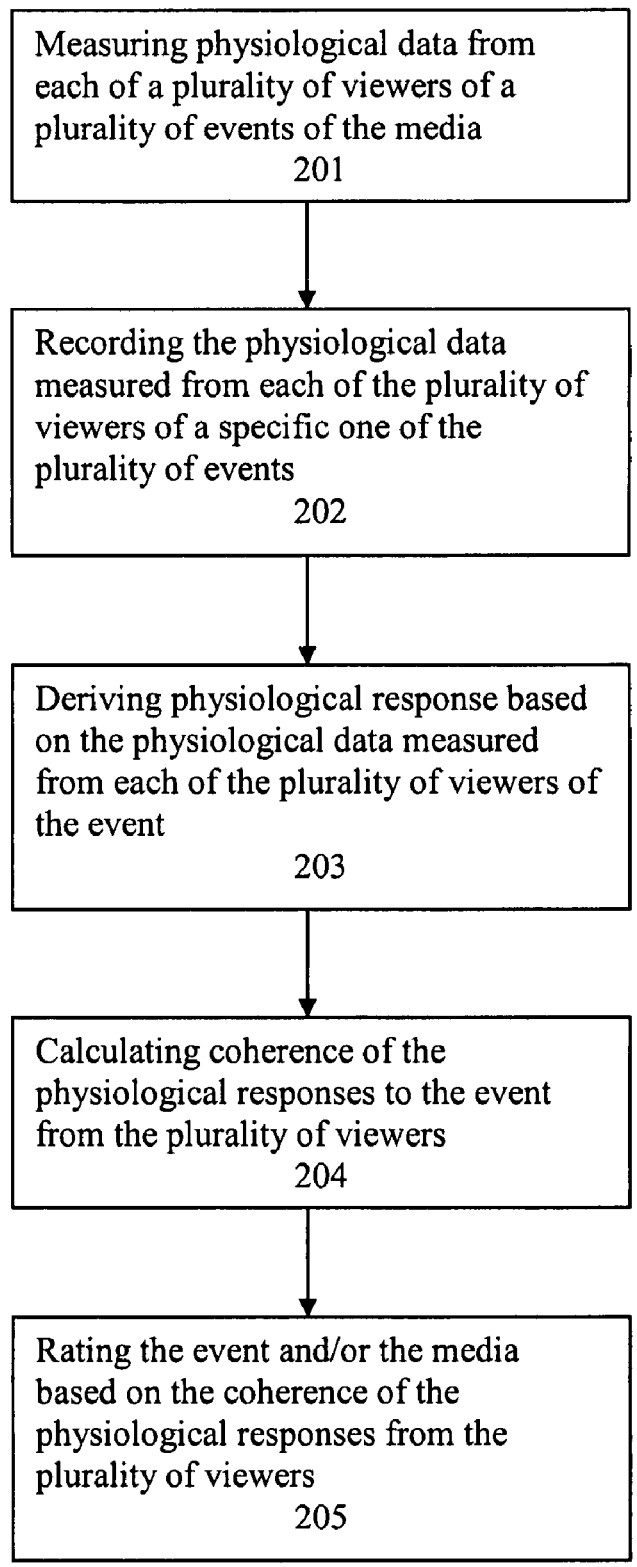
FIG. 2 is a flow chart illustrating an exemplary process for rating a media based on coherence of physiological responses from viewers in accordance with one embodiment of the present invention.

FIG. 2 is a flow chart illustrating an exemplary process for rating a media based on coherence of physiological responses from viewers in accordance with one embodiment of the present invention. Although this figure depicts functional steps in a particular order for purposes of illustration, the process is not limited to any particular order or arrangement of steps. One skilled in the art will appreciate that the various steps portrayed in this figure could be omitted, rearranged, combined and/or adapted in various ways.

Referring to FIG. 2, physiological data from each of a plurality of viewers watching an event in a media is measured at step 201. The measured physiological data can then be recorded at step 202, and physiological responses to the event can be derived based on the physiological data measured from the viewers of the event at step 203. At step 204, coherence of the viewers' physiological responses to the event is calculated, and the event and/or the media can be rated based on the coherence of the physiological responses from the plurality of viewers at step 205.

Figure 3:
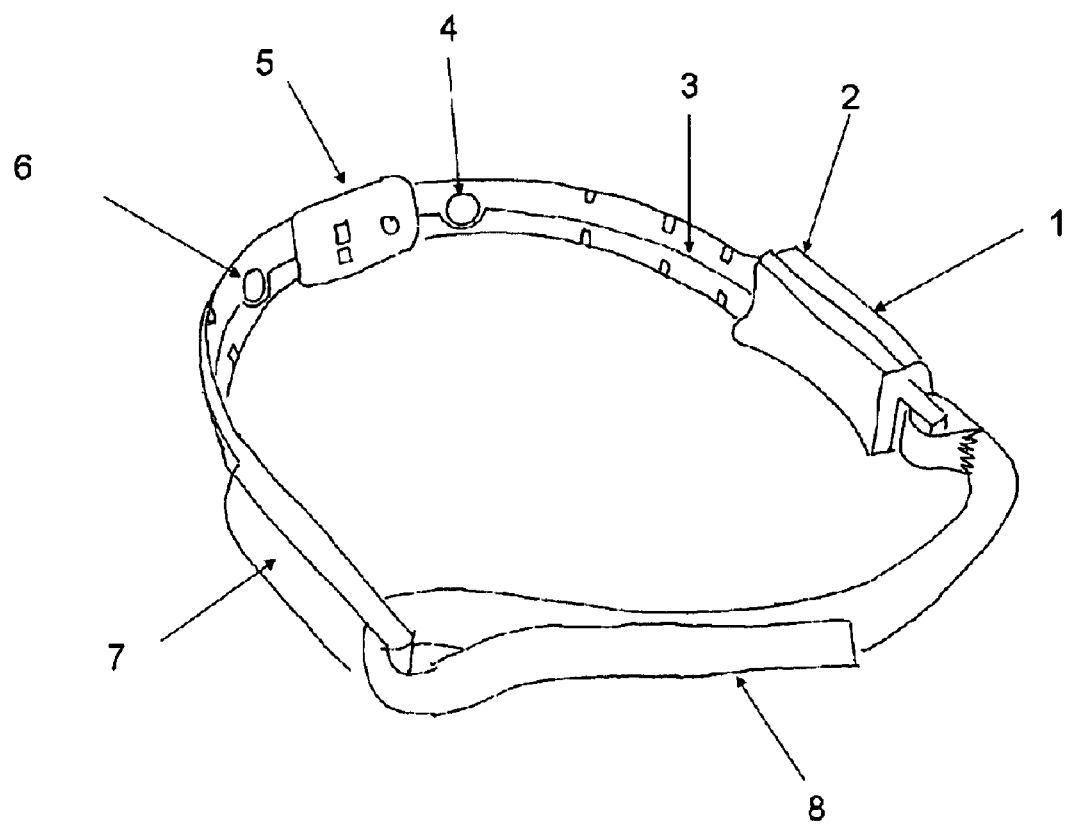
FIG. 3($a$)-($c$) show an exemplary integrated headset used with one embodiment of the present invention from different angles.
Figure 3:
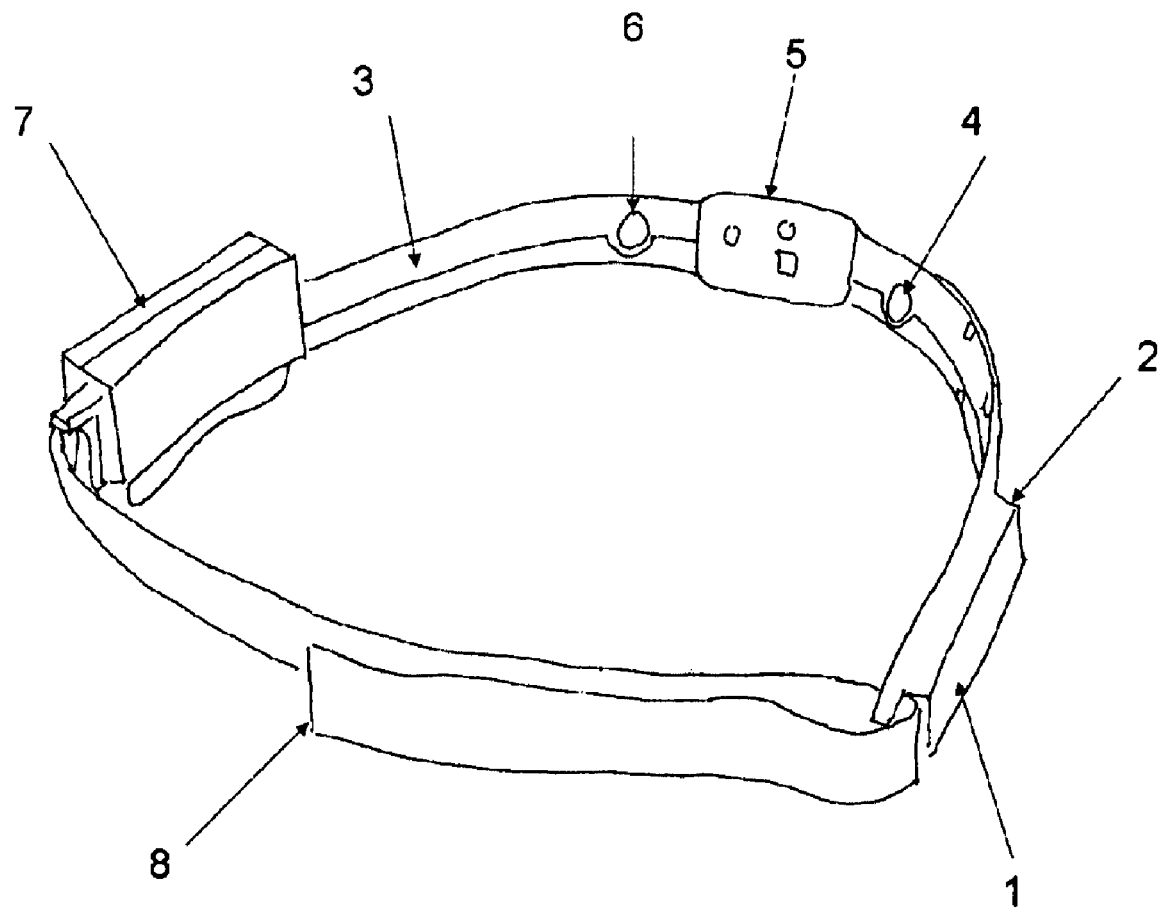
Figure 3:
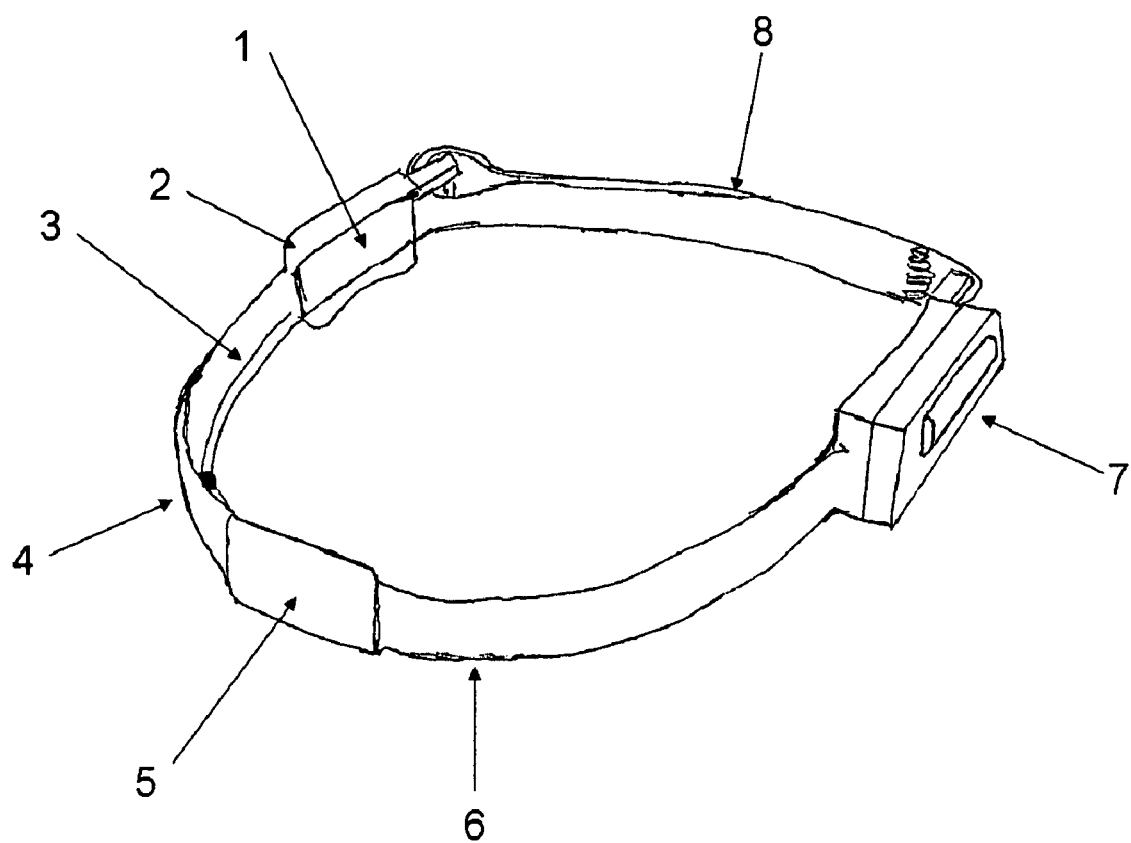

In some embodiments, an integrated headset can be placed on a viewer's head for measurement of his/her physiological data while the viewer is watching an event of the media. The data can be recorded in a program on a computer that allows viewers to interact with media while wearing the headset. FIG. 3(a)-(c) show an exemplary integrated headset used with one embodiment of the present invention from different angles. Processing unit 301 is a microprocessor that digitizes physiological data and then processes the data into physiological responses that include but are not limited to thought, engagement, immersion, physical engagement, valence, vigor and others. A three axis accelerometer 302 senses movement of the head. A silicon stabilization strip 303 allows for more robust sensing through stabilization of the headset that minimizes movement. The right EEG electrode 304 and left EEG electrode 306 are prefrontal dry electrodes that do not need preparation to be used. Contact is needed between the electrodes and skin but without excessive pressure. The heart rate sensor 305 is a robust blood volume pulse sensor positioned about the center of the forehead and a rechargeable or replaceable battery module 307 is located over one of the ears. The adjustable strap 308 in the rear is used to adjust the headset to a comfortable tension setting for many different head sizes.

In some embodiments, the integrated headset can be turned on with a push button and the viewer's physiological data is measured and recorded instantly. The data transmission can be handled wirelessly through a computer interface that the headset links to. No skin preparation or gels are needed on the viewer to obtain an accurate measurement, and the headset can be removed from the viewer easily and can be instantly used by another viewer. No degradation of the headset occurs during use and the headset can be reused thousands of times.

In some embodiments, the viewers' physiological responses can be derived via a plurality of formulas, which use the physiological data of the viewers as inputs. Facial expression recognition, "knob" and other measures of emotion can also be used as inputs with comparable validity. Each of the derived physiological responses, which can include but are not limited to, "Engagement," "Adrenaline," "Thought," and "Valence," combines physiological data from multiple sensors into a multi-dimensional, simple-to-understand, representation of viewers' emotional response.

Figure 4:
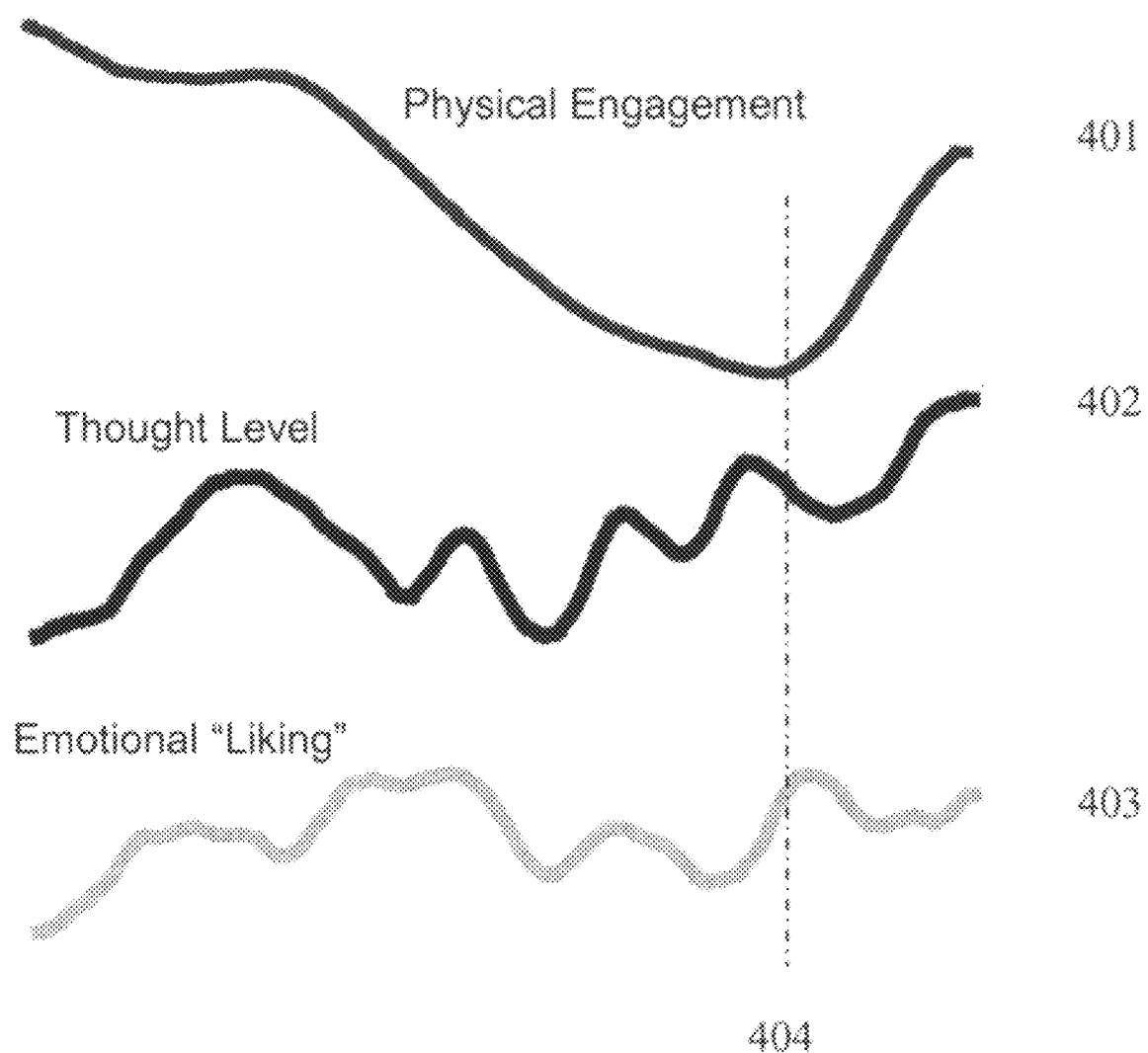
FIG. 4 shows exemplary time series plots of the average position of three physiological response vectors over time in accordance with one embodiment of the present invention.

In some embodiments, the physiological responses can be calculated across many different viewers as they are watching the same media, either at the same time or at different times. The physiological responses can be treated as a time series for each viewer, and can be combined for multiple viewers to show aggregate responses. The physiological responses can also be averaged or viewed over sections of the data to analyze the responses to key events in the media. As a non-limiting example, FIG. 4 shows exemplary time series plots of the average positions of three physiological response vectors (over time), Physical Engagement vector 401, Thought Level vector 402, and Emotional "Liking" vector 403, as 40 people watch the same commercial, Budweiser: Fixing Leak. The Physical Engagement vector 401 shows viewers relaxing as they watch the media until the point 404 at which the man falls through the roof. At this point, Physical Engagement jumps up. This corresponds to viewers being physically engaged more when they see the "action packed" ending of the advertisement as compared to the more conversation based beginning. The second vector 402 is the intensity of active thought the viewer has. The higher this value is, the more viewers will tend to remember the events.

In some embodiments, the physiological responses from viewers can be analyzed specific to the type of media the viewers are watching. For non-limiting examples:

Video Games. In the case of video games, the physiological responses and the video the viewers experience (respond to) can be overlaid and the viewers' experience can be divided into pertinent sections (events) that correspond to individual events in the game. The combination of video, key events and viewers' physiological responses allows particular instances of an event and the physiological responses across all viewers to be examined and rated.

Advertising. The key to good advertisements is making viewers remember the advertisement, like what they remembered and therefore decide to buy a product. Through sensing physiological data and tagging events, the coherence module can define which events the viewers liked, how many viewers liked each event, and divide their physiological responses into groups based on demographics to determine what the viewers were thinking on a brand moment (event) or whether the viewers liked an event better than others.

Movies. For a movie to be good, it must create the "correct" emotional response in viewers. The physiological responses to a movie can be objectively rated based on physiological data. In addition, the percentage of viewers feel about a specific moment (event) in the movie can be defined based on the coherence of viewers' responses to the event in the movie.

Coherence of Response

In some embodiments, the coherence module is operable to calculate Coherence of Response (CoR) of the viewers based on time series of physiological data recorded while the viewers are interacting with the media. Coherence of response can be calculated for all points in the time series based on how closely the trends in the responses are to each other at every given point. There are many ways to mathematically calculate the trend in the responses in a time series, which include, for non-limiting examples, the standard derivation approach and the binning approach.

In some embodiments, the coherence of the physiological responses can be calculated based on standard deviation of the physiological responses and/or standard deviation of a derivative of the physiological responses (e.g., the magnitude and value of the physiological responses) from the plurality of viewers during a specific one event. A correlation can be calculated against the derivative of all the physiological responses and the change in a trend is reflected by the number of viewers with a positive derivative of an individual response at a given time or duration of time of the event.

In some embodiments, physiological responses from the viewers to either the entire media or an event in the media can be categorized and binned into predetermined categories based on similarity of the responses. Here, the predetermined categories can include one or more of: very positive, positive, flat, negative, very negative. For a non-limiting example, responses from viewers with positive change across the event are categorized in one bin and responses from viewers with non-positive change across the event are categorized in another bin. The number/percentage of viewers that respond in one way or the other are then counted. For instance, the number of viewers responding with positive emotions to a joke (during most time of the joke) are counted and compared to the number of viewers responding without positive emotions to the same joke. Other embodiments utilize different bins or different response data, including small/large deviation where small and large are defined by being below and above a predetermined number.

Once the physiological responses from the viewers are binned, the overall coherence of the responses to the event and/or the media can be rated based on the distribution of number of viewers in each response bin. In some embodiments, the percentage of viewers responding with a positive response change is used to rate an event. For a non-limiting example, if 80% of viewers respond positively to a joke, the joke is considered as successful. Other embodiments aggregate the ratings across many events (e.g. the percentage of events with over 70% coherence in change) and other metrics.

Figure 5:
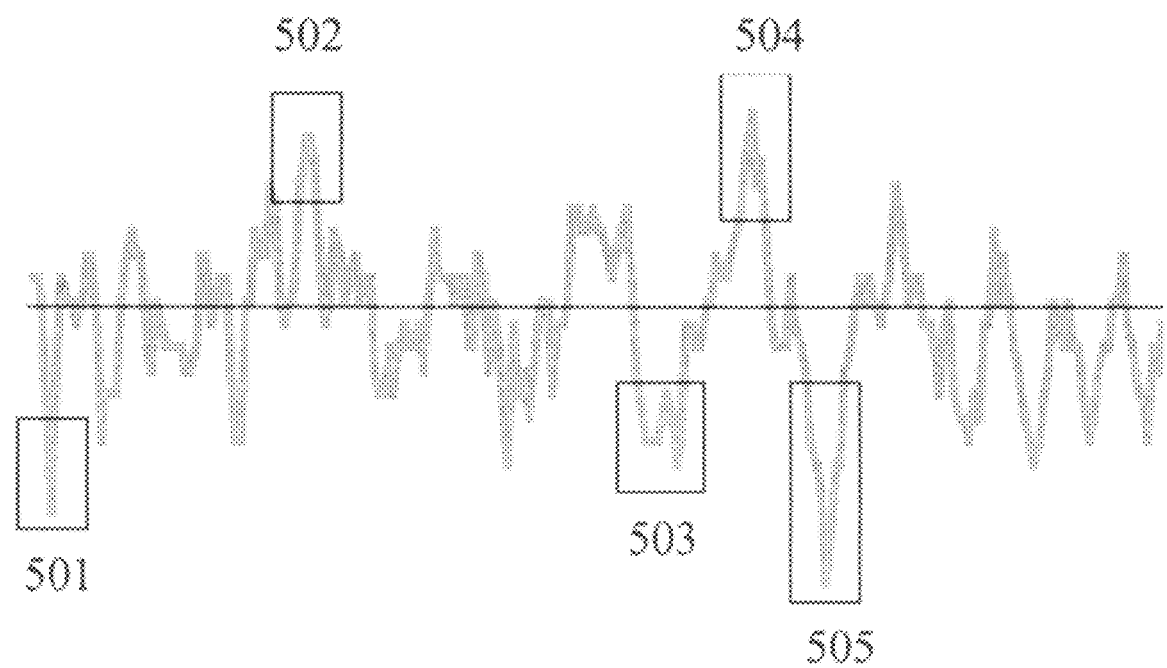
FIG. 5 is an exemplary graph showing coherence of physiological responses for the liking of an advertisement as calculated from physiological data of 40 people watching an advertisement in accordance with one embodiment of the present invention.

As a non-limiting example, FIG. 5 is an exemplary graph showing coherence of physiological responses for the liking of an advertisement as calculated from physiological data of 40 people watching the Gillette Fusion Super Bowl advertisement from 2006. The 5 boxes show areas of high positive and negative coherence during the session of the advertisement. Coherence in this instance is calculated as the number of viewers with a positive or negative derivative at every 0.25 second section of the advertisement. Boxes 501, 503, and 505 show coherence of response when liking is dropping over most people. Positive areas (boxes 502 and 504) show coherence of response when liking is rising over most people. The most coherent response happens in boxes 504 and 505, where box 504 happens at second 35 of the advertisement, directly before the Gillette Fusion logo is introduced, and box 505 happens directly after the logo is introduced. From this analysis, a conclusion can be deduced that there is a very positive build up to the product introduction but then viewers have a negative response to the introduction.

In some embodiments, time series of physiological data can also be smoothed and filtered prior to CoR calculations to allow for different scales of responses to be calculated. For a non-limiting example, if the physiological data is recorded at 100 Hz, but a calculation for a long event (e.g., 2 minutes) is needed, the high frequency data can be removed, allowing the information in the data to be of the same order of magnitude in frequencies as the length of calculation. In addition, if CoR needs to be calculated over a short period of time (e.g., a few seconds), the low frequency components of the signals can be removed to minimize the influence of prior events that could affect the position of the data. This approach will line up the data between viewers and allow only the pertinent data to be used in the CoR calculation.

Rating Media with CoR

Once CoR are calculated at every point in the time series of physiological responses for a set of physiological responses to an event, a rating can be created for the event and/or the media via one or more of the following:

Absolute CoR Score. One embodiment of the present invention uses an absolute CoR score as calculated by the mathematical implementation of coherence of the physiological responses. This allows for absolute comparison between events in the media.

Normalized CoR Score. Another embodiment of the present invention calculates a normalization factor for CoR Score ratings based on a set of data from prior tests. This allows a piece of media to be measured on a scale relative to comparable data (e.g., same genre, same advertising campaign, same set of video game levels), and percentile ratings can be created. For a non-limiting example, Movie X is in the 95% percentile of CoR scores, which is very good, while Movie Y is in the 55% of movie scores, meaning that viewers do not feel the same emotions as much in Movie X and consequently Movie Y will not do as well as Movie X in the market place.

Graded CoR Score. In some embodiments, grade level scores can also be created for the media, allowing for ratings of A, B, C, D, F or other comparable schemes to be used.

In some embodiments, scores can also be calculated for non-linear, or semi-linear media such as video games, websites and other interactive media in addition to scores calculated based on a time series that is constant between viewers. The time series for each viewer can be divided into events that appear across all viewers. Such events include but are not limited to fight scenes in video games, explosions, viewing the home page on a website, going to a chapter of a DVD and any other ones.

In some embodiments, the coherence module can create an overall rating for CoR by averaging the magnitude of the CoR values of various events in the entire media in order to compare the strength of different events in the media:

$$\text{Overall } CoR = \sum_{t=0}^{T} \frac{|CoR(t)|}{T}$$

Non-linear weights can also be placed on the CoR value:

$$\text{Overall } CoR = \sum_{t=0}^{T} \frac{|f(CoR(t))|}{T}$$

Here, f(x) can be a function such as log, polynomials or other ones:

$f(x)=x^2$ $f(x)=x^3$ $f(x)=x^2+x$ $f(x)=\log(x)$

Here, the function can change the characteristics of the data, which greatly increases the differentiation seen in the score. This pertains to low coherence scores, such as 10% coherence being classified as very low, and high coherence scores such as 70% coherent being classified as very good. By using a function such as $f(x)=x^2$, these two values will be very strongly differentiated, making the 10% value only 0.01 and the 70% value 0.49, or 5 times bigger. This differentiates high coherence points from low coherence points, penalizing a media more for being low coherence and helping a media for being high coherence. Overall, CoR score is a value that can be used to compare the experience and strength of multiple events in the media and other metrics of this kind. The higher this value is, the more coherent the media is.

The coherence of responses to each instance of an event can then be calculated via the same mathematical formulas, with the period of calculation being the length of the event instead of increments of time. The outcome of this will be a rating of responses to each event. For a non-limiting example, if 70% of events where a video game player for game X interacted with boss monster X lead to a rise in engagement, while 90% of interactions with boss monster Y lead to rises in engagement, boss monster Y has a more coherent response than boss monster X. Such calculation can be done for every pertinent event in the piece of media and these scores can then be combined to create overall scores.

In some embodiments, the coherence module can create a more complete measure of the coherence of the experience by combining the CoR values for multiple vectors of physiological responses:

Full Emotional CoR=$CoR_{Liking}$+$CoR_{Thought}$+ $CoR_{Physical\ Engagement}$+...

This full CoR value over multiple vectors of physiological responses, which are a more complete version of the measure, takes into account the different dimensions of the media. If the media is thought provoking, creates the same positive and negative responses, and engages viewers in the same way, the media will be powerful and will do well in the market. The reason to look at a specific subset of individual vectors is to measure dimensions of the experiences of the viewers. If every viewer thinks at the same point (event) in the media, but has different emotional liking values, the conclusion is that while the media made viewers think, their responses to the media were very different emotionally, with some having a positive and some a negative response.

In some embodiments, the coherence module is further operable to group the plurality of viewers by one or more of race, gender, age, demographics, income, habits, and interests and associate and/or compare the rating of the specific one event and/or the media according to such grouping of the plurality of viewers.

Figure 6:
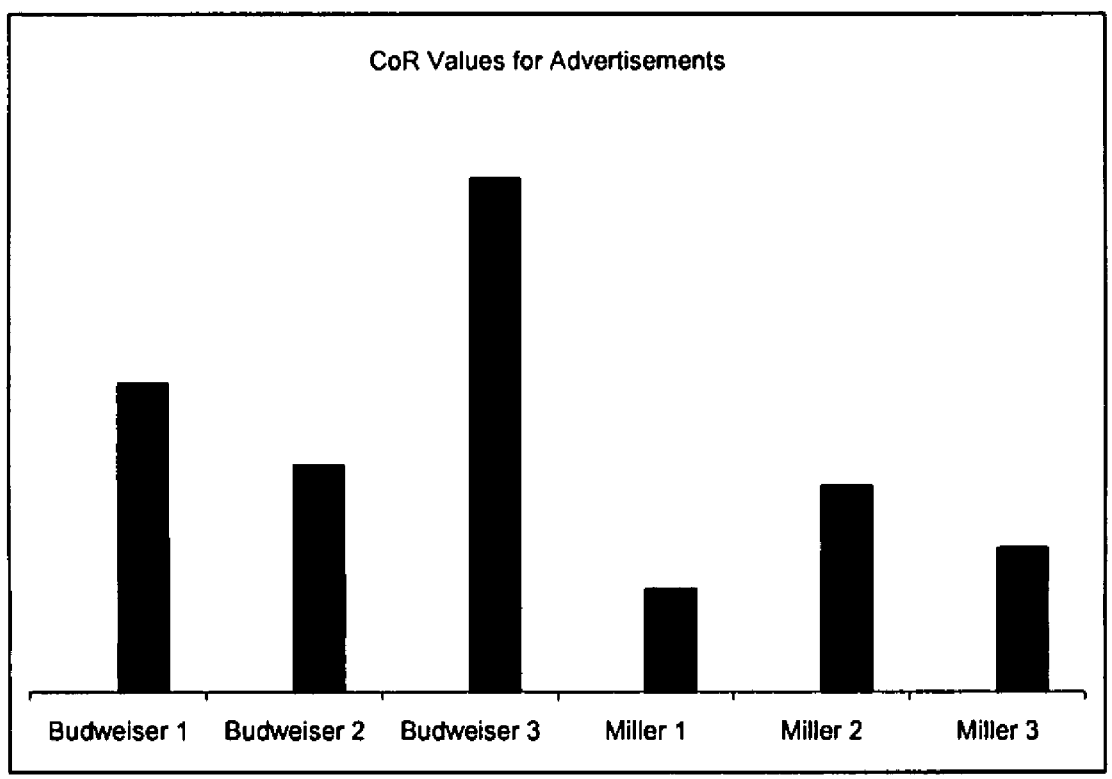
FIG. 6($a$)-($b$) show exemplary coherence of response (CoR) values for advertisements and video games, respectively, in accordance with one embodiment of the present invention.
Figure 6:
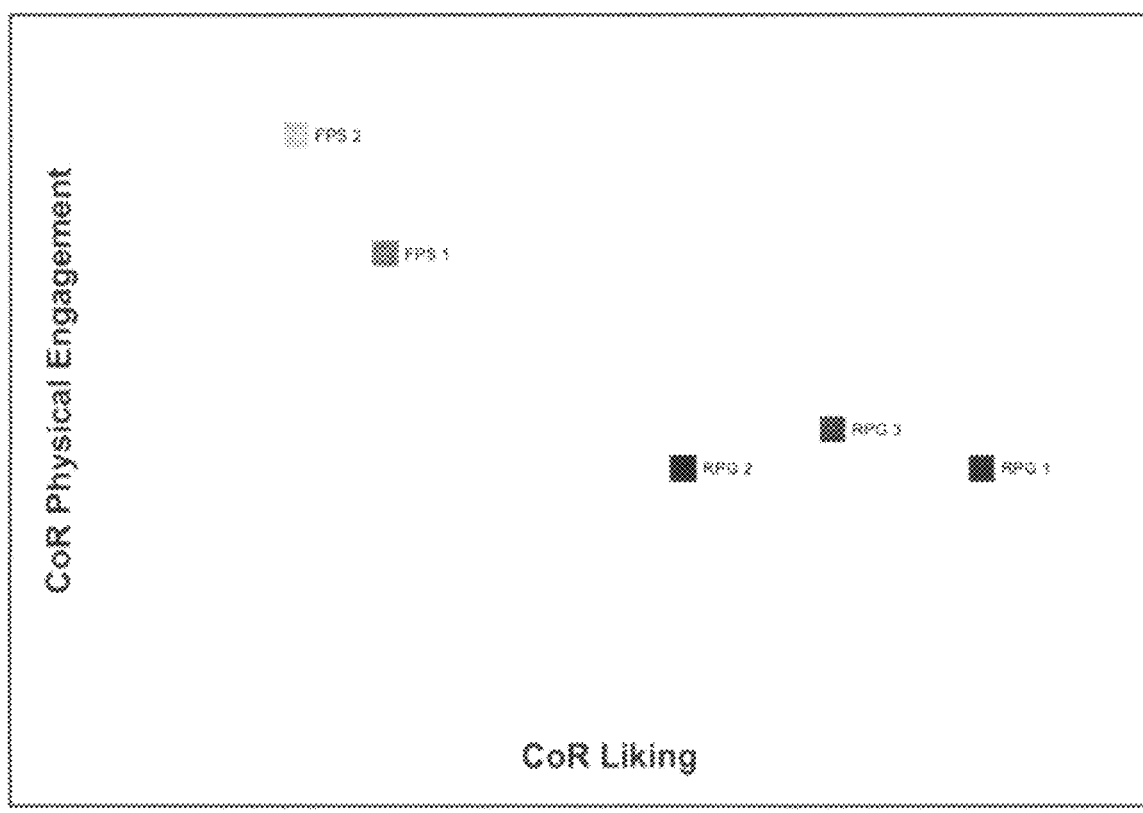

There are many ways to view these measures/ratings of events and media, from a list of CoR values, to graphs, to scatter plots that include multiple CoR dimensions and/or multiple events of the media whose CoR values are plotted. As a non-limiting example, FIG. 6(a) shows exemplary CoR values for 6 advertisements: Budweiser 1-3 and Miller 1-3. It can be seen that the Budweiser advertisements have much higher CoR values than the Miller ones, which correlates to Budweiser's better performance in the market place. As another non-limiting example, FIG. 6(b) shows exemplary CoR values for Liking and Physical Engagement for 5 video games: FPS 1-2 and RPG 1-3. The roll playing games (RPG) are heavy on plot and are very good at creating emotional responses in players, as evidenced by their position of high CoR scores in Liking. In the other dimension, Physical Engagement, their CoR Score is much lower due to the more incoherent emotions of random skirmishes that are not always intense. In contrast, the first person shooter (FPS) games are very good at creating a coherently intense experience across players, but they do not create the positive and negative emotions in players as coherently, leading to their higher Physical Engagement CoR scores and low Liking CoR scores.

One embodiment may be implemented using a conventional general purpose or a specialized digital computer or microprocessor(s) programmed according to the teachings of the present disclosure, as will be apparent to those skilled in the computer art. Appropriate software coding can readily be prepared by skilled programmers based on the teachings of the present disclosure, as will be apparent to those skilled in the software art. The invention may also be implemented by the preparation of integrated circuits or by interconnecting an appropriate network of conventional component circuits, as will be readily apparent to those skilled in the art.

One embodiment includes a computer program product which is a machine readable medium (media) having instructions stored thereon/in which can be used to program one or more computing devices to perform any of the features presented herein. The machine readable medium can include, but is not limited to, one or more types of disks including floppy disks, optical discs, DVD, CD-ROMs, micro drive, and magneto-optical disks, ROMs, RAMs, EPROMs, EEPROMs, DRAMs, VRAMs, flash memory devices, magnetic or optical cards, nanosystems (including molecular memory ICs), or any type of media or device suitable for storing instructions and/or data. Stored on any one of the computer readable medium (media), the present invention includes software for controlling both the hardware of the general purpose/specialized computer or microprocessor, and for enabling the computer or microprocessor to interact with a human viewer or other mechanism utilizing the results of the present invention.

Such software may include, but is not limited to, device drivers, operating systems, execution environments/containers, and applications.

The foregoing description of the preferred embodiments of the present invention has been provided for the purposes of illustration and description. It is not intended to be exhaustive or to limit the invention to the precise forms disclosed. Many modifications and variations will be apparent to the practitioner skilled in the art. Particularly, while the concept "module" is used in the embodiments of the systems and methods described above, it will be evident that such concept can be interchangeably used with equivalent concepts such as, class, method, type, interface, bean, component, object model, and other suitable concepts. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

What is claimed is:

1. A system to support rating media, comprising:
   an interface to obtain physiological data from each of a plurality of viewers watching a plurality of events of the media; and
   a coherence module to:
      derive a physiological response for each viewer of the plurality of viewers based on the physiological data measured from each viewer watching a specific one of the plurality of events;
      calculate a coherence of change corresponding to a plurality of the physiological responses of the plurality of viewers and the specific one event, wherein the coherence module is to calculate the coherence of change based on a closeness of trends in the physiological responses of the plurality of viewers at each point of the measure of the physiological data; and
      rate at least one of the specific one event or the media based on the coherence of change of the plurality of the physiological responses of the plurality of viewers.

2. The system of claim 1, comprising an integrated sensor headset including one or more sensors to measure the physiological data.

3. The system of claim 2, wherein the one or more sensors include one or more of an electroencephalogram, an accelerometer, a blood oxygen sensor, a galvanometer, or an electromyograph.

4. The system of claim 2, wherein the integrated sensor headset comprises one or more of:
   one or more axis accelerometers;
   one or more EEG electrodes;
   one or more heart rate sensors; or
   a processing unit.

5. The system of claim 1, wherein the media comprises at least one of a movie, a video, a television program, a television commercial, an advertisement, a video game, interactive online media, a print or any other media from which a viewer can learn information or be emotionally impacted.

6. The system of claim 1, wherein a duration of each of the plurality of events of the media is constant, non-linear, or semi-linear in time.

7. The system of claim 1, wherein the physiological data comprises one or more of heart rate, EEG signals, blink rate, breathing, or motion.

8. The system of claim 1, wherein the physiological response comprises one or more of thought, liking, engagement, immersion, physical engagement, valence, or vigor.

9. The system of claim 1, wherein the coherence module is to record the physiological data measured from each of the plurality of viewers of the specific one event.

10. The system of claim 1,
    wherein the coherence module is to:
    bin the physiological responses to the specific one event from the plurality of viewers into a plurality of categories based on similarity of the physiological responses; and
    calculate a coherence of change corresponding to a plurality of the physiological responses based on a percentage of the physiological responses showing a positive change in each of the plurality of categories.

11. The system of claim 10, wherein the plurality of categories include one or more of very positive, positive, flat, negative, or very negative.

12. The system of claim 10, wherein the coherence module is to rate the specific one event as high if most of the physiological responses fall in a single one of the plurality of categories.

13. The system of claim 10, wherein the coherence module is to rate the specific one event as low if most of the physiological responses fall in multiple of the plurality of categories.

14. The system of claim 1, wherein the coherence module is to rate the specific one event as high if most of the plurality of viewers feel a same way about the event.

15. The system of claim 1, wherein the coherence module is to rate the media based on ratings of the plurality of events of the media.

16. The system of claim 1, wherein the coherence module is to rate at least one of the specific one event or the media via one or more of an absolute score, a relative score to a comparable media, or a graded score.

17. The system of claim 1, wherein the coherence module is to:
    group the plurality of viewers by one or more of race, gender, age, demographics, income, habits, or interests; and
    one or more of associate or compare the rating of at least one of the specific one event or the media according to such grouping of the plurality of viewers.

18. The system of claim 1, wherein the coherence module is to rate the specific one even as low if most of the plurality of viewers feel differently about the event.

19. A system comprising:
    an interface to obtain physiological data from each of a plurality of viewers watching a plurality of events of the media; and
    a coherence module to:
       derive a physiological response for each viewer of the plurality of viewers based on the physiological data measured from each viewer watching a specific one of the plurality of events;
       remove high or low frequency portions of the physiological data measured based on a duration of the specific one event;
       calculate a coherence of change corresponding to a plurality of the physiological responses of the plurality of viewers and the specific one event; and
       rate at least one of the specific one event or the media based on the coherence of change of the plurality of the physiological responses of the plurality of viewers.

20. A system comprising:
an interface to obtain physiological data from each of a plurality of viewers watching a plurality of events of the media; and
a coherence module to:
derive a physiological response for each viewer of the plurality of viewers based on the physiological data measured from each viewer watching a specific one of the plurality of events; and
calculate a coherence of change corresponding to a plurality of the physiological responses based on a standard deviation of a derivative of the physiological responses over the specific one event from the plurality of viewers, wherein the derivative comprises a magnitude of the physiological response and the coherence of change is based on the viewers with a positive derivative.

21. A method to support rating media, comprising:
obtaining physiological data from a plurality of viewers watching a plurality of events of the media;
deriving physiological responses for viewers of the plurality of viewers based on the physiological data measured from the viewers watching a specific one of the plurality of events;
calculating a coherence of change corresponding to a plurality of the physiological responses of the plurality of viewers and the specific one event, wherein the calculating of the coherence change is based on a closeness of trends in the physiological responses of the plurality of viewers at points of the measure of the physiological data; and
rating at least one of the specific one event and the media based on the coherence of change of the physiological responses of the plurality of viewers.

22. The computing method of claim 21, comprising recording the physiological data measured from the plurality of viewers of the specific one event.

23. The computing method of claim 21, comprising removing high or low frequency portions of the physiological data measured based on a duration of the specific one event.

24. The computing method of claim 21, further comprising calculating the coherence of the physiological responses based on one or more of a standard deviation or a standard deviation of a derivative of the physiological responses of the physiological responses over the specific one event from the plurality of viewers.

25. The computing method of claim 21, comprising:
binning the physiological responses to the specific one event from the plurality of viewers into a plurality of categories based on similarity of the physiological responses; and
calculating the coherence of the physiological responses based on percentage of the physiological responses showing a positive response change in the plurality of categories.

26. The computing method of claim 25, comprising rating the specific one event as high if most of the physiological responses fall in a single one of the plurality of categories.

27. The computing method of claim 21, comprising rating the specific one event as high if most of the plurality of viewers feel a same way about the specific one event.

28. The computing method of claim 21, comprising rating the media based on ratings of the plurality of events of the media.

29. The computing method of claim 21, comprising rating at least one of the specific one event or the media via one or more of an absolute score, a relative score to comparable media, or a graded score.

30. The computing method of claim 21, comprising:
grouping the plurality of viewers by one or more of race, gender, age, demographics, income, habits, or interests; and
one or more of associating or comparing the rating of at least one of the specific one event or the media according to such grouping of the plurality of viewers.

31. A tangible machine readable disc or memory comprising instructions stored thereon, which when executed, cause a machine to at least:
obtain physiological data from a plurality of viewers watching a plurality of events of the media;
derive physiological responses for the plurality of viewers based on the physiological data measured from a set of the viewers watching a specific one of the plurality of events;
calculate a coherence of change corresponding to a plurality of the physiological responses of the plurality of viewers and the specific one event, the calculating of the coherence change being based on a closeness of trends in the physiological responses of the plurality of viewers at points of the measure of the physiological data; and
rate at least one of the specific one event and the media based on the coherence of change of the physiological responses of the plurality of viewers.

* * * * *

UNITED STATES PATENT AND TRADEMARK OFFICE
CERTIFICATE OF CORRECTION

| | | |
|---|---|---|
| PATENT NO. | : 8,230,457 B2 | Page 1 of 1 |
| APPLICATION NO. | : 11/804517 | |
| DATED | : July 24, 2012 | |
| INVENTOR(S) | : Hans Lee et al. | |

It is certified that error appears in the above-identified patent and that said Letters Patent is hereby corrected as shown below:

Col. 11, Claim 21 should read as follows:

21. A method to support rating media, comprising:
    obtaining physiological data from a plurality of viewers watching a plurality of events of the media;
    deriving physiological responses for viewers of the plurality of viewers based on the physiological data measured from the viewers watching a specific one of the plurality of events;
    calculating a coherence of change corresponding to a plurality of the physiological responses of the plurality of viewers of the specific one event, wherein the calculating of the coherence change is based on a closeness of trends in the physiological responses of the plurality of viewers at points of the measure of the physiological data; and
    rating at least one of the specific one event and the media based on the coherence of change of the physiological responses of the plurality of viewers.

Signed and Sealed this
Eleventh Day of September, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,230,457 B2 | Page 1 of 1 |
| APPLICATION NO. | : 11/804517 | |
| DATED | : July 24, 2012 | |
| INVENTOR(S) | : Hans Lee et al. | |

It is certified that error appears in the above-identified patent and that said Letters Patent is hereby corrected as shown below:

Col. 11, lines 18-34, Claim 21 should read as follows:

21. A method to support rating media, comprising:
    obtaining physiological data from a plurality of viewers watching a plurality of events of the media;
    deriving physiological responses for viewers of the plurality of viewers based on the physiological data measured from the viewers watching a specific one of the plurality of events;
    calculating a coherence of change corresponding to a plurality of the physiological responses of the plurality of viewers of the specific one event, wherein the calculating of the coherence change is based on a closeness of trends in the physiological responses of the plurality of viewers at points of the measure of the physiological data; and
    rating at least one of the specific one event and the media based on the coherence of change of the physiological responses of the plurality of viewers.

This certificate supersedes the Certificate of Correction issued September 11, 2012.

Signed and Sealed this
Ninth Day of October, 2012

David J. Kappos
*Director of the United States Patent and Trademark Office*